(12) United States Patent
Fantini et al.

(10) Patent No.: US 8,588,368 B2
(45) Date of Patent: Nov. 19, 2013

(54) MACHINE FOR INTRAOPERATIVE RADIATION THERAPY

(75) Inventors: Mario Fantini, Rome (IT); Vincenzo Iacoboni, Rome (IT); Aquilino Gava, S.Vendemiano (IT)

(73) Assignee: Sordina S.p.A., Vicenza (IT)

( * ) Notice: Subject to any disclaimer, the term of this patent is extended or adjusted under 35 U.S.C. 154(b) by 315 days.

(21) Appl. No.: 12/773,841

(22) Filed: May 4, 2010

(65) Prior Publication Data

US 2010/0278305 A1 Nov. 4, 2010

Related U.S. Application Data

(62) Division of application No. 10/515,991, filed as application No. PCT/IT03/00336 on May 29, 2003, now abandoned.

(30) Foreign Application Priority Data

May 31, 2002 (IT) .............................. RM2002A0301

(51) Int. Cl.
*A61N 5/10* (2006.01)
(52) U.S. Cl.
USPC ............................... 378/65; 250/492.3; 600/1
(58) Field of Classification Search
USPC ........ 600/1–8; 250/492.1–504 H; 378/64, 65, 378/119–161
See application file for complete search history.

(56) References Cited

U.S. PATENT DOCUMENTS

| | | | | | |
|---|---|---|---|---|---|
| 3,720,817 | A | * | 3/1973 | Dinwiddie | ........................ 600/1 |
| 4,589,810 | A | * | 5/1986 | Heindl et al. | ...................... 414/5 |
| 4,629,938 | A | * | 12/1986 | Whitham | ...................... 315/5.41 |
| 5,635,721 | A | * | 6/1997 | Bardi et al. | ................. 250/492.3 |
| 6,069,938 | A | * | 5/2000 | Chornenky et al. | ........... 378/122 |

FOREIGN PATENT DOCUMENTS

| GB | 1 386 318 | * 3/1975 |
|---|---|---|
| WO | WO 00/74072 | * 12/2000 |

* cited by examiner

*Primary Examiner* — John Lacyk
*Assistant Examiner* — Carrie R Dorna
(74) *Attorney, Agent, or Firm* — Abe Hershkovitz; Hershkovitz & Associates PLLC

(57) ABSTRACT

Machine for intraoperative radiation therapy or IORT (Intra Operative Radio Therapy), comprising a body, a radiating head (23) connected to the body, and a shield for X rays. The shield comprises a mobile stand (29) supporting an absorbing mass (13), which is coupled, through connecting means (32), to means (33) for detecting the position of the absorbing mass (13), apt to give to a processor at least a signal indicating the position of the absorbing mass (13) with respect to the body of the machine. The processor determines, on the basis of the position and/or the orientation of the radiating head (23), the position of the absorbing mass (13) with respect to the electron beam axis.

13 Claims, 5 Drawing Sheets

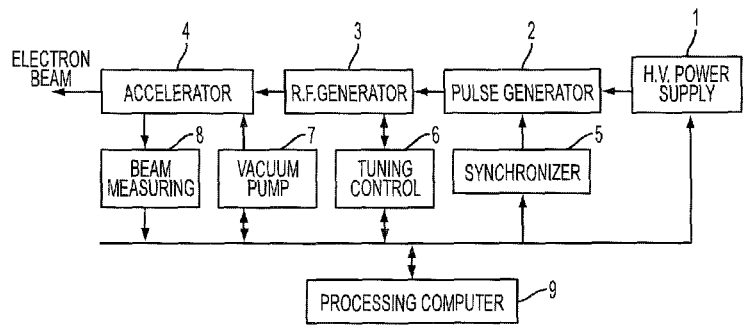
FIG. 1
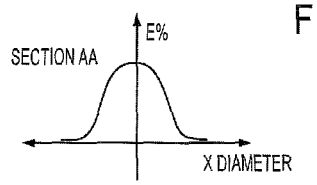
FIG 2a - PRIOR ART
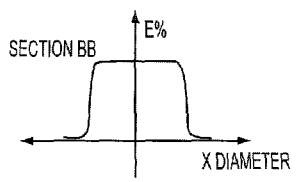
FIG. 2b - PRIOR ART
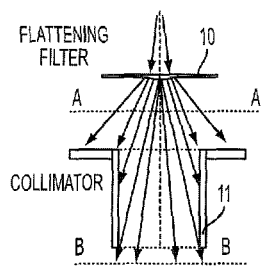
FIG. 2c - PRIOR ART
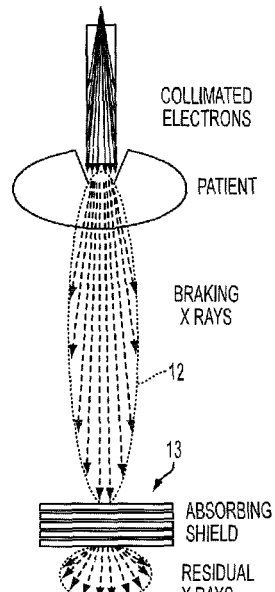
FIG. 3

FIG. 5 - PRIOR ART

MACHINE FOR INTRAOPERATIVE RADIATION THERAPY

RELATED APPLICATIONS

This Application is a divisional Application of U.S. application Ser. No. 10/515,991, filed Jul. 20, 2005 now abandoned, entitled "MACHINE FOR INTRAOPERATIVE RADIATION THERAPY", which is a U.S. National Stage of PCT/IT03/00336 filed on May 29, 2003, which claims priority to Italian application RM2002A000301 filed on May 31, 2002, the disclosures of which are specifically incorporated herein in their entireties by specific reference thereto.

FIELD OF THE INVENTION

The present invention concerns a machine for intraoperative radiation therapy or IORT (Intra Operative Radiation Therapy) which is easily movable, having reduced weight and size, and which makes possible, in a reliable, simple and efficient way, to radiate an electron beam drastically reducing the diffusion of X rays, accurately controlling environmental radiation, and very precisely measuring the radiation dose.

It is known that Intraoperative Radiotherapy consists in treating the patient with ionizing radiations in the course of the surgical operation. IORT, initially developed by some, mainly Japanese and US, research institutes, since the 1960's to the 1980's, began to ripen in the following decade, with the creation of a specific international society, the ISIORT, and increasingly participated biennial meetings methodically following one another.

However, in the mid-1990's the conviction spread among the experts that IORT would have remained the prerogative of large university centers which could face the big logistical costs that IORT involved. In fact, out of the institutions dedicated to research, it could not be proposed to invest considerable amounts of money for a therapy that, due to limited figures, could not produce statistically reliable data. Hence, IORT remained a branch of excellence performed by researchers who tried to find a standardization in order to have data which were comparable and therefore apt to be added among different centers. The main reason for constituting the ISIORT intraoperative radiotherapy international society was in fact creating a common and commonly accepted reference point issuing protocols and procedures eliminating the local particular differences which inevitably were set up.

For radiating a particular organ which is exposed due to the surgical opening, it is not convenient to use X rays which are commonly used for conventional radiotherapy; in fact these are highly penetrative and once aimed at the area to be treated they involve everything being along their aiming direction, distributing undesired radiation doses also to other organs which are thereby damaged.

Instead, IORT uses a beam of electrons, which are the primary particles being accelerated in order to obtain, after a conversion, the X rays. In fact, the electrons are slightly penetrative ionizing radiations and their penetration is precisely controlled through the kinetic energy that they are given by the accelerator. A cursory empirical rule establishes that the electrons penetrate in a biological tissue for a number of centimeters equal to their kinetic energy, expressed in MeV, divided in half; hence, a 6 MeV beam shall be completely absorbed within the first 3 centimeters of tissue.

Hence, the use of electrons takes away from the danger of damaging organs beneath the bottom of the tumor bed which is exposed by the surgeon. Moreover, the electron beams, thanks to the reduced penetration, are easily shaped and transversely limited, being thereby possible to treat only parts to be radiated, reducing the morbidity induced by applications of considerable doses such as the ones used in IORT.

The doses normally used in conventional radiotherapy range from 25 to 75 Gray, where 1 Gy=1 Joule/1 Kg. These doses are delivered to the patient by a series of usually biweekly applications, of 1-2 Gy per application. In IORT typical doses range from 10 to 25 Gy, applied only once. It is evident that an error in dosimetry in IORT may be much more dangerous than in classical radiotherapy. Therefore, apparatus dedicated to IORT has to detect very precisely the dose of electron radiancy.

The shape of beams is obtained by making the electron beam pass within an applicator made by a tube in plastic material having a wall thickness of the order of 5-8 millimeters. This thickness is generally sufficient to prevent accelerated particles from spreading outside the beam. Beam shape is generally circular, and rarely polygonal.

When it was initially developed, IORT was performed by moving the anesthetized patient from surgical room to radiotherapy bunker where there was the accelerator that was prearranged to emit electrons (the accelerator is usually an X ray source); the electron beam was applied through applicators in light material capable to shape and limit the beam itself. In order to eliminate or at least minimize patient movement, some institutes have built surgical rooms next to or within the radiotherapy bunker; in any case these were an extremely expensive solution which have in fact limited the diffusion of IORT.

Hence, a procedure IORT comprises the following steps:
conventional surgical operation;
preparing the patient for transport;
transporting the patient;
preparing the patient for radiation;
treatment with electrons; and
ending the surgical operation.

From an electromagnetic point of view, a machine for radiotherapy is very similar to a radar transmitter, since it is substantially a very short pulse transmitter, pulses having a duration of 1÷5 μsec, and very powerful, having a power of the order of 2÷5 MW, operating in the microwave range, with frequency of the order of 3 Ghz corresponding to a wavelength $\lambda=10$ cm. This microwave pulse enters an accelerator comprising a series of cavities, which may be resonant or aperiodic, where it generates extremely strong instantaneous electric fields which cause a beam of charged particles, i.e., electrons, to be accelerated due to electrostatic attraction.

With reference to FIG. 1, a high voltage power supply 1 transforms the line voltage into a continuous voltage, having a value ranging from 9 to 18 kV, which charges a system of capacitors wherein the energy needed to generate a single pulse is stored. Through a suitable switch called a thyratron, a pulse generator 2 transforms the previously stored energy into a pulse having a short duration, equal to about 1÷5 μsec, and a voltage of the order of 50 kV.

This pulse is applied to a microwave generating thermionic tube 3, called a magnetron, that transforms it into a train of electromagnetic oscillations which are inputted into an accelerating structure 4 for carrying out the accelerating process of an electron beam.

For a proper operation, all the mentioned devices need auxiliary circuits and apparatus which provide for proper operation or for stabilizing the whole system depending on the circumstances.

In particular, a synchronizer 5 comprises a set of circuits producing the pulses that make all the pulse devices of the pulse generator 2 coordinately work, providing for their proper operation sequence. A tuning control circuit 6 provides for keeping resonance frequency of magnetron 3 in step with the frequency needed for a proper operation of the accelerator. A vacuum pump 7 maintains a ultra high vacuum level, of the order of $10^{-8}$ hPa (hectoPascal), within the accelerating structure 4, which is essential in order that the acceleration process occurs without impediments due to an excessive impact of particles with gas molecules within the accelerating structure 4. A system 8 for measuring the energy quantity conveyed by the beam and that is incident on the tissues of the patient allows the emitting process to be stopped when the radiated energy quantity reaches a value which is sufficient for the desired therapeutic purposes. Finally, a processing computer 9 controls the operations of the machine.

The conventional machines for radiotherapy present some drawbacks.

First of all, as it has been already observed, they do not satisfy the requirement for mobility, also because the apparatus is heavy and bulky.

In fact, in case of an immobile machine for radiotherapy, even if it is placed within a surgical room, the patient must be moved in order to be positioned under it. This implies a complex and difficult logistic organization, since the above is a procedure which is extraneous to the normal conduct of a surgical operation, and a time extension of the anesthesia, further causing a physical stress for the patient.

Moreover, the immobile machine placed in a surgical room may treat patients at a frequency equal to the one of the surgical operation, that is, typically, one patient per day for abdominal applications and up to three per day in case of mammary tumors. However, the time of real use is greatly shorter, since the radiation lasts about one minute and the whole operation of positioning and subsequent removal of the patient does not generally reach 15 minutes. Hence, this results in keeping mostly unused a machine potentially capable of treating a high number of patients.

Although some mobile machines for radiotherapy have been developed, these have drawbacks due to weight and size and to the need of calibration after movements.

Moreover, a machine, either immobile or mobile, is driven onto the patient to be radiated by a radiotherapy technician skilled in driving, who is, however, not sterile, since he has to handle objects, such as the remote control, which cannot be sterilized. The machine is considered sterile only for the applicator portion fixed thereto. The positioning of the machine consists in joining the two portions of the applicator (one of which is positioned in contact with the surgical opening of the patient, and the other one is connected to the machine). The technician controlling this action cannot get close to the patient, since he is not sterile, and he is therefore led through vocal instructions by the (sterile) radiotherapist who is close to the patient. This procedure is quite dangerous, because the one driving the machine has a very limited sight of the operating zone and there is the risk of hitting or compressing the patient's internal organs which are quite fragile.

Further drawbacks of the known machines for radiotherapy are due to the system for diffusing the electron beam.

In fact, the accelerated electron beam leaves the vacuum environment of the accelerating structure emerging through a titanium thin foil, which is interposed in order to keep the vacuum level within the structure sealed. The transverse size, that is the diameter, of the beam at the moment of leaving are of the order of a millimeter. Thanks to the electrostatic repulsion among the electrons and to the diffusion with the air, the beam opens with an angle depending on the beam power that, at 10 MeV, is of the order of ±10° around the geometric axis.

As shown in FIG. 2a, when the energy conveyed by the beam is analyzed according to relative units by sectioning it with a plane containing the axis, a Gaussian type distribution is obtained. In order to be usable on the patient, the beam has instead to have a constant value in the whole range of application, as shown in FIG. 2b. For obtaining such a transformation, as shown in FIG. 2c, the beam is diffused by making it cross a metallic plate 10 having variable thickness and sectioning it with a light material tube 11, capable to absorb the undesired side portion of the beam.

However, such a beam flattening solution is inadequate for machines for Intraoperative Radiotherapy, since the diffusing plate 10 produces a significant quantity of braking X rays which permeate the surgical room environment and are difficult to be shielded. This imposes a noticeable shielding which causes high values of the machine weight, making the use of special floors necessary.

In this regard, the problem of environmental radiation in the surgical room is particularly important.

Besides the already mentioned X radiations due to the diffusing filters crossing, the environmental radiations which are present during operation of an electron accelerator for IORT in the surgical room comprise electron radiations due to electrons leaving the collimator, also known as secondary electrons, and X radiations generated by the patient, i.e. the electron beam braking radiations due to the fact that the patient brakes the electron beam absorbing almost its whole energy.

The secondary electron radiations, even being of noticeable number, have a very low energy, estimated in few keV, and generally remained confined within the surgical room. It is therefore sufficient to leave the room during radiation.

However, the warning and control procedures are not completely accurate.

The braking X radiations are the most harmful and inevitable. The percentage of beam energy which is converted into X rays amounts to 0.3% of the incident energy, the generated X radiations having energy ranging from 0 to the energy of the most energetic electron. As shown in FIG. 3, from a geometric point of view the radiation is extremely anisotropic, having a lobe 12 along the running direction of the original electron beam. The aperture of the lobe 12 is very restricted and at an angle of a few degrees deviating from the axis, its intensity is halved, while at 90° its intensity is reduced to one hundredth of the value on the axis. This remarkable anisotropy makes possible an effective beam, interposing an absorbing mass 13 along the beam axis prolongation so as to prevent the radiation from propagating outside the surgical room. The absorbing mass 13 is made of lead slabs. Considering that the decivalency thickness (that is the thickness of material reducing to one tenth the intensity of the incident beam) at the energies normally used in IORT is equal to 4 cm, in order to attenuate the incident radiation by a factor ranging from 50 to 1000, the thickness of the absorbing mass 13 normally ranges from 6 and 12 centimeters.

However, while in the case of immobile machines for radiotherapy, the absorbing mass 13 is oriented in a fixed position with respect to the accelerator axis. In the case of mobile machines for radiotherapy, the correct positioning of the absorbing mass 13 is not simple, taking also into account the accuracy imposed by the law for the safety of the operators.

A further drawback present in known machines for radiotherapy is due to the system for measuring the beam, needed in all the accelerators for radiotherapy in order to determine that the prescribed dose quantity has been really delivered by the machine and to stop delivering.

In fact, transmission ionization chambers are commonly used, which are crossed by the radiation beam. The chamber is made of two foils of a conductor which is very thin (so as to not attenuate the beam) and spaced 1-2 millimeters and between which a potential difference of some hundreds of volts is maintained. The particles, either electrons or photons, crossing the space between the foils ionize an amount of air molecules proportionally to their own kinetic energy and to their number. The ionized molecules are hence attracted by the negative electrode while the electrons, which are stripped from the external orbits, migrate to the positive electrode; this current which is generated by the passage of the beam is collected by a capacitor and is transformed in a charge amount which is measured by a suitable circuit. Considering that the dose flow is equal to the ratio of pulse dose to pulse duration, the ionization chambers remain linear with dose flows of the maximum order of about 100 Gy/sec, beyond which the flow generates a number of electrons and ionized molecules so high that these recombine before reaching the ionization chamber electrodes, therefore subtracting a charge amount from the measure. Microscopically this effect is translated into a progressive desensitization of the chambers up to being no more usable.

In case of mobile machines for Intraoperative Radiotherapy, in order to maintain an environmental radiation quantity minimum, the electron beam is not diffused and must be measured, for reasons of efficient machine architecture, directly at the accelerator output, where it still has transverse size of the order of a few millimeters. Since the typical flow of the mobile machine for Intraoperative Radiotherapy is of the order of 20,000 Gy/sec, the ionization chambers operate in a very low sensitivity region that does not allow them to appreciate variations lower than some point percent. Considering that the precision limit of clinical dosimetry is of the order of 2%, it is evident that the transmission ionization chambers are unusable.

The solution which is used in some mobile machines is to employ a scattering filter so as to lower the electron current by a factor ranging from 10 to 40 and prevent the transmission chambers from being affected by noticeable recombination phenomena. However, such a solution implies a very high environmental radiation quantity which imposes the use of a circular attenuator (a sort of collimator for the diffusion) in heavy material (depleted uranium). The use of such a shielding causes the radiating head to be heavy and, due to balancing reasons, this propagates in cascade on the weights of the whole machine.

A further drawback of the known machines for radiotherapy is due to the accelerating structure.

With reference to FIG. 4, the accelerating structure is composed by a series of resonant cavities 14 coupled among them, which are equivalent to a series of elementary oscillating pure resonant circuits, comprising an inductor L and a capacitor C, coupled between them. In this circuit, the resonance frequencies of the elementary cells are adjusted so as to have a 90° phase displacement between the voltages at the capacitors of two contiguous cells.

With reference to FIG. 5, it may be observed that the accelerating structure cavities are of two types which alternately follow: accelerating cavities 15 and coupling cavities 16. In particular, the accelerating cavities 15 have a large inductance and a small capacitance; their configuration comprises central protrusions 17 which are the capacitive component, around which it is formed the electric field that is used to do the acceleration work. Vice versa, the coupling cavities 16 have a large capacitance and a small inductance; their function is to transfer the radiofrequency (RF) energy by displacing its phase by 90°, without participating in the accelerating process. In order to adjust accurately the resonance frequencies, the accelerating structure comprises tuning micrometer screws 18 which vary the volume of the accelerating and coupling cavities 15 and 16.

However, the presence of tuning screws 18 creates a significant technological difficulty as far as the vacuum level is concerned.

In fact, within the accelerating structure, the ultrahigh vacuum level, of the order of $10^{-8}$ hPa, has to be maintained and in order to obtain it, it is necessary for a pump to be continuously operating for the whole operative life of the accelerator. Hence, each tuning screw 18 has to be accurately sealed by a suitable vacuum brazing. This involves the necessity to heat the whole structure up to temperatures of the order of 500-600° C. These thermal cycles, besides being expensive, since they conspicuously extend the production time of the accelerator, also tend to make the building material get relaxed and, hence, to vary its physical size, thus impairing the precision of tuning.

SUMMARY OF THE INVENTION

It is therefore an object of the present invention to provide a machine for IORT which is easily movable and positionable.

It is still an object of the present invention to provide such a machine which makes possible, in a reliable, simple and efficient way, to radiate an electron beam by drastically reducing the diffusion of X rays, while accurately controlling and shielding environmental radiation.

It is a further object of the present invention to provide such a machine which makes possible to measure very precisely the radiation dose.

It is also an object of the present invention to provide such a machine which is technologically simple to be realized.

The specific subject matter of this invention is a machine for intraoperative radiation therapy or IORT (Intra Operative Radiation Therapy), comprising a mobile body, provided with at least two driving wheels and at least an idle wheel, each driving wheel being operated by a corresponding moving engine, the machine further comprising a radiating head connected to the body, configured to emit an electron beam, the machine being characterized in that it further comprises handling devices which are integral with the radiating head, an engine for moving the radiating head, configured to impart to the radiating head at least a vertical translation motion, said handling devices comprising at least three bidirectional sensors, configured to measure both a traction stress and a compression stress, each one of which sends to a control processor an electric signal which is proportional to a measured stress which is orthogonal to the sensor, said control processor operating the moving engines of each of said at least two driving wheels and the engine for moving the radiating head proportionally to the stresses which are measured by at least three bidirectional sensors.

Also according to the invention, the engine for moving the radiating head may be configured to impart to the radiating head may be a rotational motion on at least a plane, said handling devices may comprise at least four bidirectional sensors, and the control processor may operate the moving engines of each of at least two driving wheels and the engine for moving the radiating head on the basis of an orientation of the handling devices.

Still according to the invention, the engine for moving the radiating head may be configured to impart to the radiating head a pitch rotational motion and a roll rotational motion, said handling devices comprising at least five bidirectional sensors.

Furthermore according to the invention, said control processor may perform the following operations:

determining the orientation of the handle with respect to a first Cartesian triad which is integral with the body of the machine, composing the stresses which are measured by the bidirectional sensors, obtaining a resulting vector and a resulting torque with respect to a second Cartesian triad which is integral with the handling devices, calculating the projections of the resulting vector and of the resulting torque onto the first fixed Cartesian triad, obtaining a vector of translation of the body, a torque of rotation of the body, a vector of vertical translation of the radiating head, a torque of roll rotation of the radiating head, and a torque of pitch rotation of the radiating head; and operating the moving engines of each of at least two driving wheels, so as to move the body linearly and proportionally to the vector of translation of the body and to rotate the body proportionally to the torque of rotation of the body, and operating the engines for moving the radiating head, so as to translate the radiating head proportionally and vertically to the vector of vertical translation of the radiating head, to impart a roll rotation to the radiating head proportionally to the torque of roll rotation of the radiating head, and to impart a pitch rotation proportionally to the torque of pitch rotation of the radiating head.

Preferably according to the invention, each one of at least three bidirectional sensors is formed by a pair of opposed sensors, each of which is configured to measure a compression stress which is orthogonal to it.

Also according to the invention, each one of the compression stress sensors may be inserted in a mechanical housing, provided with elastic means, mobile between a first unstressed limit position and a second limit position of maximum stress onto the sensor, wherein the maximum stress onto the sensor is not larger than the full scale of this.

Still according to the invention, each one of at least two driving wheels may be provided with a clutch which is configured to uncouple the wheel from the respective engine making it idle.

Furthermore according to the invention, the machine may comprise housing compartments which are sealed against external humidity.

Preferably according to the invention, the machine has a weight lower than 400 Kg and/or a width not larger than 100 cm, more preferably not larger than 80 cm, and a length not longer than 2.5 meters, more preferably not longer than 2 meters.

Also according to the invention, the machine may be provided with a system for diffusing the electron beam, leaving an accelerating structure, which comprises a divergent magnetic lens, configured to make the trajectories of the electrons crossing it diverge. In particular, such a system for diffusing the electron beam may be applied also to machines for IORT different from the one which is the specific subject of the present invention.

Still according to the invention, the machine may be provided with a timer configured to operate an acoustic device for a duration T, preferably adjustable, before the start of the electron beam emission.

Furthermore according to the invention, the machine may be provided with a shield for X rays comprising a mobile stand supporting an absorbing mass, which is coupled, through connecting devices, to devices for detecting the position of the absorbing mass, and configured to give to a processor at least a signal indicating the position of the absorbing mass with respect to the body of the machine, said processor determining, on the basis of the position and/or the orientation of the radiating head, the position of the absorbing mass with respect to the electron beam axis.

Preferably according to the invention, the processor is the control processor which receives the electrical signals of the stresses measured by the bidirectional sensors.

Also according to the invention, the detecting devices may comprise two potentiometers configured to detect the azimuth angle and the distance of the center of the absorbing mass with respect to the body of the machine.

Still according to the invention, the connecting device comprises an anchorage dome of the detecting devices.

Furthermore according to the invention, the mobile stand may be provided with lockable wheels.

Also according to the invention, the absorbing mass may be mobile with respect to the mobile stand through a sliding device.

Still according to the invention, the processor receiving at least a signal indicating the position of the absorbing mass with respect to the body of the machine may be configured to drive a luminous device for signaling the necessary movements for correctly positioning the shield and attaining the correct position of the shield.

In particular, such shield for X rays may be applied also to machines for IORT different from the one which is the specific subject of the present invention.

Furthermore according to the invention, the machine may be provided with a system for measuring the total dose of the electron beam, emitted during an IORT treatment for a period of duration R, comprising an amperometric transformer, configured to measure the instantaneous current $I_{beam}$ of the emitted electron beam, the instantaneous dose D being calculated as a function of the instantaneous current $I_{beam}$, the total dose being calculated through a time integration of the instantaneous dose for the treatment period.

Also according to the invention, the instantaneous dose D may be calculated on the basis of a quadratic dependency from the instantaneous current $I_{beam}$: $D=K*I_{beam}^2$ or alternatively on the basis of a linear dependency from the instantaneous current $I_{beam}$, $$D=D_0+A*\Delta I_{beam}$$

where $\Delta I_{beam}=I_{beam}-I_{beam\_Ref}$, wherein $I_{beam\_Ref}$ is a reference value of the instantaneous current of the emitted electron beam, and the coefficients $D_0$ and A are experimentally determined in a phase of clinical dosimetry of the machine.

In particular, such system for measuring the total dose of the electron beam may be applied also to machines for IORT different from the one which is the specific subject of the present invention.

Still according to the invention, the electron beam may come out from an accelerating structure comprising a tuning device, placed in corresponding slots of the accelerating structure, said tuning device being directly and locally welded to the accelerating structure onto each of the slots by electrical arc welding in a controlled atmosphere.

Furthermore according to the invention, the accelerating structure may present, in correspondence of each slot, a profile configured to dissipate heat.

Also according to the invention, the tuning device may comprise a tuning screw covered by a cap.

BRIEF DESCRIPTION OF THE DRAWINGS

The present invention will be now described, by way of illustration and not by way of limitation, according to its preferred embodiments, by particularly referring to the Figures of the enclosed drawings, in which:

FIG. 1 shows an electromagnetic block diagram of a machine for IORT;

FIG. 2a shows the profile of the energy conveyed by the electron beam at the output of an accelerating structure;

FIG. 2b shows the profile of the energy conveyed by the electron beam which is necessary for an IORT treatment;

FIG. 2c shows an electron beam diffusion system used in the machines of the prior art;

FIG. 3 shows a geometrical section draft of radiations generated during an IORT treatment;

FIG. 5 shows a particular accelerating structure of the prior art;

DETAILED DESCRIPTION OF PREFERRED EMBODIMENTS

In the following description, same references will be used to indicate similar elements in the Figures.

The machine for IORT according to the invention has a considerable mobility. In particular, the preferred embodiment has a weight lower than 400 Kg, eliminating any problem in floor statics and, most of all, in capacity of elevators and vehicles; moreover, it has reduced sizes, having a width of 80 cm, in order to make possible movement through elevator doors, and a length not larger than 2 meters; still, the turning radius is such to allow the machine to rotate around a vertical axis placed within the same machine; finally, the preferred embodiment of the machine is provided with autonomy of movement so that it can move without the necessity to be supplied with electric power during a transfer.

The machine for IORT according to the invention allows a sterile person, for example the radiotherapist, to control movement directly. This mobility can be obtained with a "sterile handle", whose mechanical stresses caused by the operator's hand are translated into electrical signals controlling the movements of the machine so as to follow the same stresses.

Figure 4:
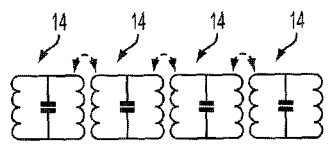
FIG. 4 shows a circuit which is equivalent to an accelerating structure.
Figure 6:
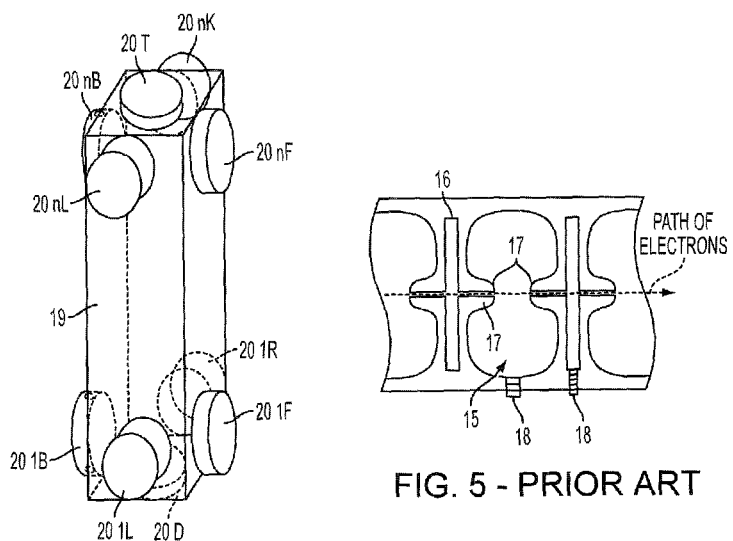
FIG. 6 shows a schematic perspective view of the handling device of a preferred embodiment of the machine according to the invention.
Figure 7:
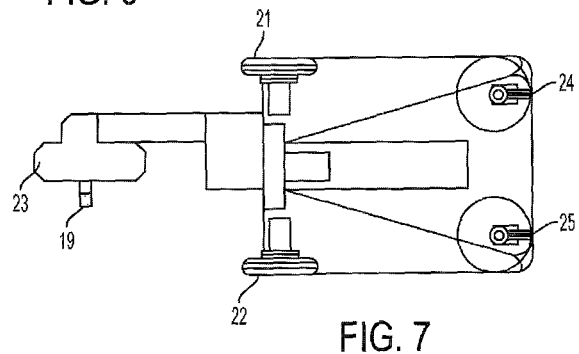
FIG. 7 shows a bottom plan view of a preferred embodiment of the machine according to the invention.

With reference to FIG. 6, from a mechanical point of view, the handle of the preferred embodiment of the machine is like a prism 19 suspended from ten stress sensors 20, which translate the stress caused by the operator's hand into electrical signals which, after being interpreted by a control processor, not shown, generate mechanical movements configured to nullify the same stress. In particular, with reference to FIG. 7 the processor operates two, respectively right and left, moving engines of the machine which act on the two front wheels, respectively right 21 and left 22, of the machine, and engines for moving the radiating head 23 of the machine, from which the electron beam comes out. The sterile handle is placed in correspondence with the radiating head 23. The machine still comprises two rear wheels, respectively right 24 and left 25, which are idle and pivoting. Preferably, the two driving wheels 21 and 22 are provided with a clutch, that may be operated through a suitable tool, which uncouples them from the respective engine and makes them idle; this makes possible a rapid pushing motion in case of shutdown or failure. Moreover, the machine is provided with engine supplying batteries which make it autonomous during transfers.

Thanks also to the independence of the two driving wheels 21 and 22, the servomechanism formed by the ten sensors 20, the processor, the two moving engines of the machine and the engines for moving the radiating head 23 of the machine allows the machine to have five degrees of freedom:
rectilinear motion of the whole machine onto a plane,
rotational motion of the whole machine onto a plane,
vertical translation motion of the radiating head 23,
roll motion of the radiating head 23, and
pitch motion of the radiating head 23.

The ten sensors 20 form the five bidirectional sensors needed for the listed five degrees of freedom, configured to measure both the traction stress and the compression stress. For reasons of simplicity and reliability, the preferred embodiment of the machine according to the invention comprises, instead of five bidirectional sensors, ten sensors 20 configured to react only to compression stresses, being much more sturdy and precise than bidirectional sensors.

Figures 8, 9:
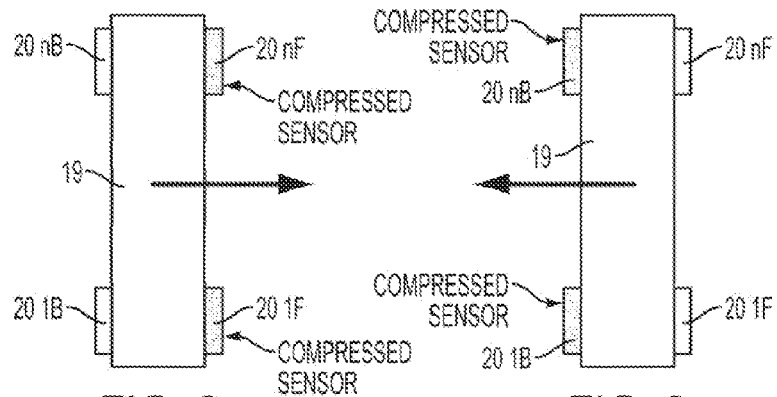
FIG. 8 shows a schematic side view of the handling device of FIG. 6 in a first stressing condition.
FIG. 9 shows a schematic side view of the handling device of FIG. 6 in a second stressing condition.

The user takes the prism 19 in correspondence of its center and may impart a force in any direction. With reference to FIG. 8, assuming that the user imparts a forward uniform stress, as indicated by the arrow in FIG. 8, the two front sensors, respectively top 20nF and bottom 20lF, are stressed, detecting a compression, and give two equal signals; in particular, in FIG. 8 the stressed sensors are shown in grey. The control processor of the servomechanism analyzes the signals coming from all ten sensors 20 and operates the two moving engines at identical speed so as to impart to the machine a forward movement. Similarly, with reference to FIG. 9, if the user imparts a rearward uniform stress, as indicated by the arrow in FIG. 9, the two rear sensors, respectively top 20nB and bottom 20/B, shown in grey, are stressed and give two equal signals that the control processor interprets for operating the two moving engines at identical speed so as to impart to the machine a left sideways movement. In particular, in the following of the present description a stress involving only two sensors 20 placed on the same side is indicated as an equally directed stress.

Still with reference to FIG. 6, it is evident that, if the equally directed stress is imparted to two side sensors, alternatively to the right sensors 20nK and 20/R or the two left sensors 20nL and 20/L, the control processor generates an inverted rotation of the two moving engines (the right engine rotates clockwise and the left one rotates anticlockwise or vice versa) which is proportional to the stress, that causes a rotation around a vertical axis which is central with respect to the segment joining the axis of the two driving wheels.

These movements may be combined in an infinite series of elementary translations and rotations, since the control processor continuously analyzes the stresses which are imparted to the prism 19 and consequently modifies the commands sent to the moving engines.

Figures 10, 11:
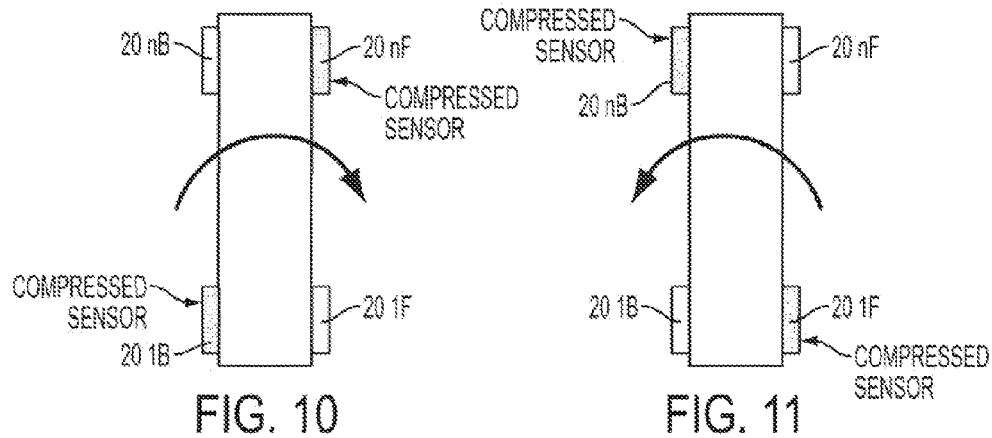
FIG. 10 shows a schematic side view of the handling device of FIG. 6 in a third stressing condition.
FIG. 11 shows a schematic side view of the handling device of FIG. 6 in a fourth stressing condition.

Differently, differential stresses on the sensors 20 produce corresponding signals that the control processor analyzes so as to operate the engines for moving the radiating head 23 of the machine which generate rotations of the radiating head 23, and precisely, depending on which pair of sensors 20 is stressed, roll or pitch rotations. In particular: in the case when the front top sensor 20nF and the rear bottom sensor 20/B are stressed, a pitch rotation is generated as shown by the arrow of FIG. 10; in the case when the front bottom sensor 20/F and the rear top sensor 20nB are stressed, a pitch rotation is generated which is the opposite of the previous one, as shown by the arrow of FIG. 11; in the case when the right top sensor 20nK and the left bottom sensor 20/L are stressed, a clockwise roll rotation is generated; finally, in the case when the right bottom sensor 20/R and the left top sensor 20nL are stressed, an anticlockwise roll rotation is generated.

Also in this case it is possible to have movements which are a combination of pitch rotations and roll rotations, that may be furthermore combined with the previously illustrated movements.

Figures 12, 13:
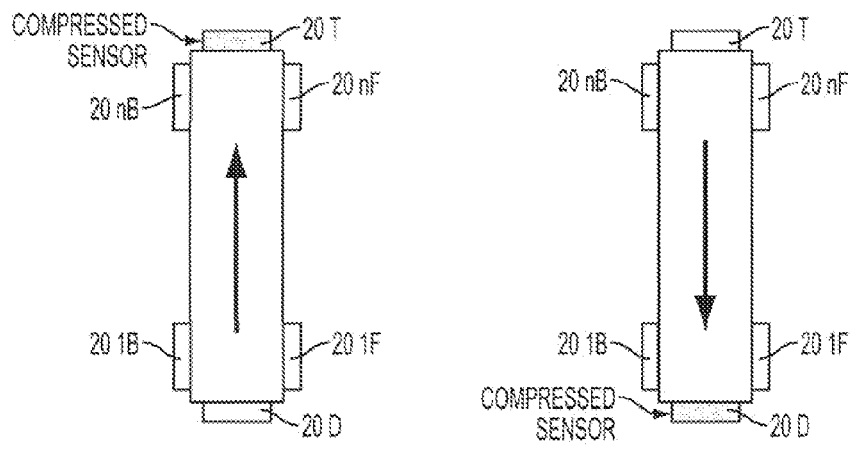
FIG. 12 shows a schematic side view of the handling device of FIG. 6 in a fifth stressing condition.
FIG. 13 shows a schematic side view of the handling device of FIG. 6 in a sixth stressing condition.

Finally, a stress on the top sensor 20T placed at the top of the prism 19 generates a lifting of the radiating head 23, as shown in FIG. 12, while a stress on the sensor 20D placed at the base of the prism 19 generates a lowering of the radiating head 23, as shown in FIG. 13.

The movements of the servomechanism, above illustrated with reference to FIGS. 8-13, are related to a configuration of the radiating head 23, to which the handle 19 is integral, placed in a vertical position, that is in a transport position. The control processor allows the machine to be correctly moved even when the radiating head 23, and consequently the axis of the prism 19, has a different orientation and, hence, the directions toward which the operator imparts motion in order to obtain a certain movement involve other sensors.

Figure 14:
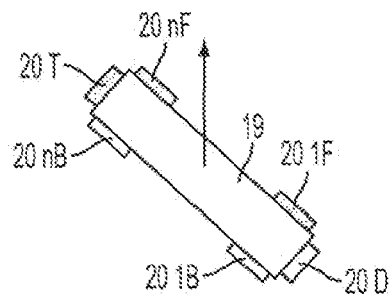
FIG. 14 shows a schematic side view of the handling device of FIG. 6 in a seventh stressing condition.
Figure 15:
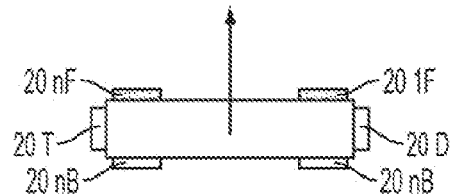
FIG. 15 shows a schematic side view of the handling device of FIG. 6 in an eighth stressing condition.

Purely by way of illustration and not by way of limitation, it is assumed that the radiating head is rotated 45° forward, as shown in FIG. 14. In order to lift it, the operator pushes upwardly the whole prism 19 which transmits the stress, besides the top sensor 20T, also to the two front sensors 20nF and 20/F, all pointed out in grey in FIG. 14. Similarly, in the limiting case (usually not possible) of the radiating head 23 and the prism 19 rotated 90°, in order to lift the head, only the front sensors 20nF and 20/F are stressed, as shown in FIG. 15.

In order to operate correctly, the engines for moving the radiating head 23 or the whole machine, the control processor performs the following operations:

determining the orientation of the prism 19 with respect to a first Cartesian triad which is integral with the machine;

composing, according to the determined orientation of the prism 19, the stresses which are measured by the sensors 20 (each one of which detects only the stresses which are orthogonal to it), until a resulting vector and a resulting torque are obtained with respect to a second Cartesian triad which is integral with the prism 19;

calculating the projections of the resulting vector and of the resulting torque onto the first fixed Cartesian triad of the machine, obtaining the vector of translation of the whole machine, the torque of rotation of the whole machine, the vector of vertical translation of the radiating head 23, the torque of roll rotation of the radiating head 23, and the torque of pitch rotation of the radiating head 23; and operating the two engines for moving the whole machine and the engines for moving the radiating head 23 proportionally to the obtained vectors and torques.

Figure 16A:
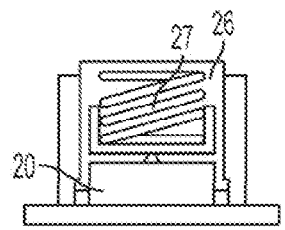
FIG. 16a shows a sectional view of a sensor of the handling device of FIG. 6 in a first configuration.
Figure 16B:
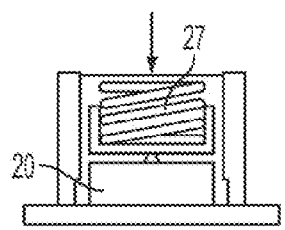
FIG. 16b shows a sectional view of a sensor of the handling device of FIG. 6 in a second configuration.

The stress sensors 20, also known as load cells, suffer from possible, even modest, overloads, because they break at a stress equal to 1.5 times their full-scale maximum charge. With reference to FIGS. 16a and 16b, in order to detect stresses which are proportional to the ones imparted by the operator, the preferred embodiment of the machine according to the invention has protection for the sensors 20. In particular, each sensor 20 is inserted into a mechanical housing 26 that, by means of a deformable elastic element 27, such as a spring, limits the accidental maximum stress that can be applied to the sensor 20. In particular, FIG. 16a shows the housing 26 in its not stressed limit position, while FIG. 16b shows the housing 26 in its limit position of maximum stress on the sensor 20. As shown in FIG. 16b, the elastic element 27 deforms up until the housing 26 reaches a mechanical stop, such as a beat with the handle structure, the maximum stress being exerted on the sensor 20 in this case being not larger than the full-scale stress on the same sensor.

Moreover, all the electronic, electromagnetic, and mechanical components of the machine, which are sensitive to humidity, are enclosed in a sealed compartment, so as to make sterilization of the whole machine in an autoclave possible.

Figure 17:
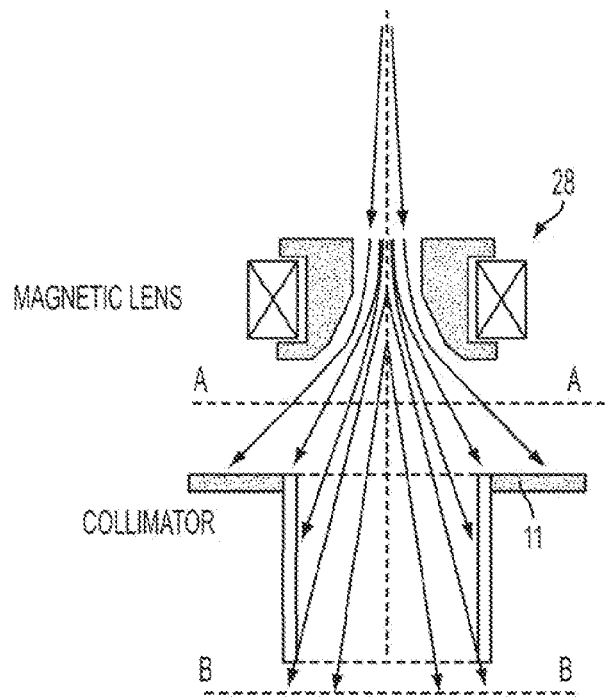
FIG. 17 shows an electron beam diffusion system of the machine of FIG. 7.

In order to make flat, instead of Gaussian, the energetic profile of the diffused electron beam and to eliminate the problem of the generation of braking X rays due to a diffusing plate, the machine for IORT according to the invention provides that the beam diffusion system comprises, as shown in FIG. 17, a divergent magnetic lens 28 for diffusing the beam. The lens 28 does not produce any radiation and is limited to make the electron trajectories diverge; in particular, a tube 11 of light material selects the diffused beam, absorbing the undesired side portion of it, obtaining the needed uniformity over the range of application, according to the profile shown in FIG. 2b.

Advantageously, the machine has luminous devices for signaling the condition of the machine on and off beam emission. Moreover, the machine may further be provided with a timer of duration T, preferably equal to 30 seconds, still more preferably adjustable, during which an acoustic device is operated to indicate the requirement of leaving the forbidden areas before the start of the beam emission. Such signaling devices facilitate the delimitation of suitable guard areas which have to be left only for the short radiating period, usually lasting 30 to 60 seconds, avoiding the use of uncomfortable and bulky mobile shields which are difficult to keep sterile.

As mentioned with reference to FIG. 3, in order to shield the braking X radiations generated by the patient, it is necessary to position an absorbing mass 13, comprising one or more lead pieces, along the beam axis prolongation.

Figure 18:
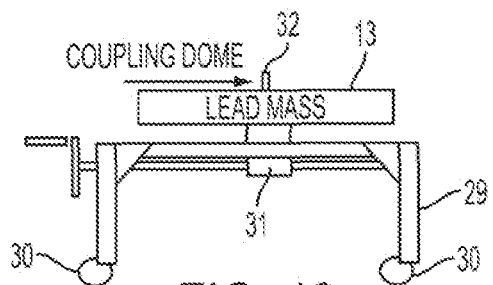
FIG. 18 shows a first detail of the X ray shield of the machine of FIG. 7.
Figure 19:
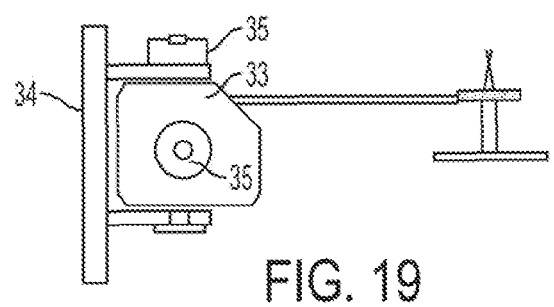
FIG. 19 shows a second detail of the X ray shield of the machine of FIG. 7.

With reference to FIGS. 18 and 19, the preferred embodiment of the machine according to the invention comprises a shield including a mobile steel stand 29, preferably provided with lockable wheels 30, to which an absorbing mass 13 is coupled and which is mobile with respect to the stand 29 by means of a sliding mechanism 31.

An anchorage dome 32 of a detecting device 33 is integrally coupled to the center of the absorbing mass 13, the detecting device 33 being integrally coupled to the machine 34, substantially at the same height as the dome 32. In particular, the detecting device 33 measures through two potentiometers 35, the azimuth angle and the distance from the center of the absorbing mass 13 with respect to the machine 34. These data, together with the elevation, the roll angle and the pitch angle of the radiating head, are processed by a processor, preferably the same control processor of the servomechanism of the machine, for unequivocally determining the position of the beam axis on the surface of the absorbing mass 13.

Figure 20:
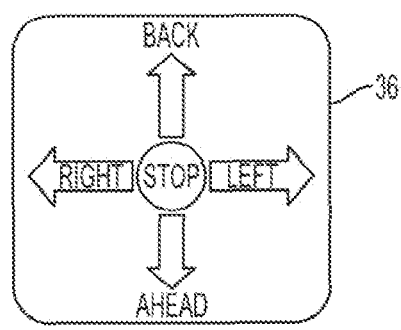
FIG. 20 shows a luminous signaling device of the machine of FIG. 7.

With reference to FIG. 20, the processor also drives a luminous signaling device 36 that gives indications to the operator for signaling the possible needed movements for correctly positioning the shield or attaining the correct position.

The preferred embodiment of the machine according to the invention further comprises a radiated beam measuring system that, instead of a transmission ionization chamber, which cannot be used for the high dose flows used for IORT, includes an amperometric transformer that measures the electron beam current at the output of the titanium window of the accelerating structure.

The electron beam energy fluency, which may be measured in terms of dose only after being absorbed by a material, is given by the product $V_{accelerating} \times I_{beam}$, where $V_{accelerating}$ is the accelerating voltage and $I_{beam}$ is the electron beam current. In the machine according to the invention, which comprises a stationary wave accelerator, the current production is related to the resonance of the cavities, like also the creation of the accelerating electric fields and, consequently, the voltage $V_{accelerating}$. Hence, assuming the electron injection constant, an equal variation of kinetic energy corresponds to a small variation $\Delta I_{beam}$ of the current $I_{beam}$. Therefore, instead of using a system for measuring the accelerating voltage $V_{accelerating}$, the measure of the dose is based on the measure of the beam current $I_{beam}$, the instantaneous dose having a dependency of quadratic type from this $$D = K^* I_{beam}^2$$

which results linearizeable for small variations $\Delta I_{beam}$ that usually are observed during the operation around the reference value $I_{beam\_Ref}$, wherein $\Delta I_{beam} \leq 0.1\ I_{beam\_Ref}$, usually plus $\Delta I_{beam} \leq 0.03\ I_{beam\_Ref}$. Therefore, the instantaneous dose D is obtained through the following linear relation from the measure of the beam current $I_{beam}$, i.e. from the variation $\Delta I_{beam}$ of this ($\Delta I_{beam} = I_{beam} - I_{beam\_Ref}$):

$$D = D_0 + A^* \Delta I_{beam}$$

where $D_0$ and A are experimentally determined in the phase of clinical dosimetry of the machine, a phase which employs dosimetries certified independently from the energy and from the dose portion, preferably according to Frike dosimetry.

The main advantage is the absolute linearity of the measuring device and the great stability and independence of the amperometric transformers from environmental factors, such as pressure, humidity and temperature. Moreover, with respect to the conventional use of transmission ionization chambers, the use of an amperometric transformer also eliminates the need for long and complex calibration measures after the movement of the machine, since an amperometric transformer is insensitive to vibrations and to acceleration due to transport.

Figure 21:
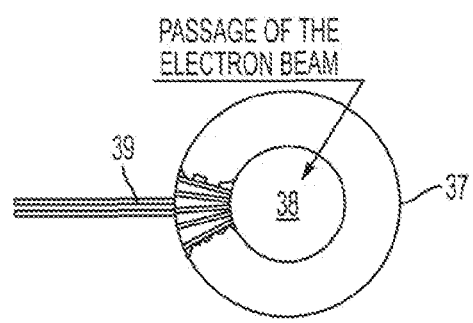
FIG. 21 shows a detail of the electron beam total dose measuring system of the machine of FIG. 7.

As shown in FIG. 21, from a constructive point of view the measuring system comprises a toroidal transformer wound on a ferrite toroidal core 37 of suitable rating: the primary of such transformer is the electron beam that, passing through the hole 38 of the torus 37 magnetically links with the wound secondary 39. The short circuit current in the secondary has a value equal to 1/n of the electron beam current $I_{beam}$, where n is the number of turns of the secondary 39 which are wound on the core 37.

Figure 22:
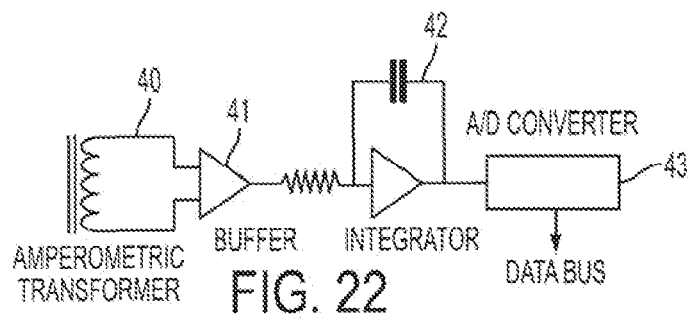
FIG. 22 shows a block diagram of the electron beam total dose measuring system of the machine of FIG. 7.

With reference to FIG. 22, the current generated on the secondary of the toroidal transformer 40, which is proportional to the current $I_{beam}$ of the beam to be measured, is inserted in a current buffer circuit 41, which is arranged to increase the impedance of the circuit downstream from the transformer 40. The output of the buffer 41 supplies an integrator circuit 42 which adds the several current contributions due to the electron beam pulses, giving at the output a voltage which is proportional to the total energy flow of the emitted electron beam. Such voltage is digitalized by an analog/digital converter or ADC 43. The output is sent to the logical circuits which carry out the comparison of the digitalized voltage with the pre-set dose value, in order to determine the moment when the irradiation process has to be stopped.

Figure 23:
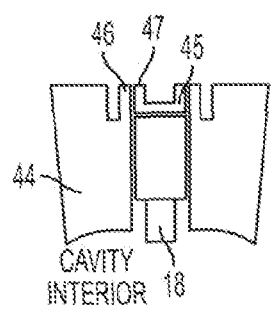
FIG. 23 shows a detail of the accelerating structure of the machine of FIG. 7.

Finally, the preferred embodiment of the machine according to the invention uses, instead of the vacuum brazing, a new seal of the tuning screw of the accelerating structure which avoids the heating of the whole structure. In particular, with reference to FIG. 23, each tuning screw 18, once inserted into the accelerating structure 44 in the adjusted final position, is covered by a cap 45, preferably in copper, which is directly and locally welded to the accelerating structure 44 on each screw 18 by arc welding in a controlled atmosphere. In order to prevent the heat from propagating, particular profiles of the structure 44 have been studied to avoid this phenomenon. In particular, the structure 44 presents, in correspondence of each slot for the screws 18, a lip 46 that is welded to the cap 45 favoring heat dissipation; also the cap 45 has a protruding frame 47 dissipating heat.

The direct and local electrical arc welding on each screw 18 in the controlled atmosphere shortens about one third the accelerator manufacturing time and presents the great advantage of allowing, in case of a loss of a seal of the tuning screw 18, the defect to be corrected by passing the electrical arc again only onto the defective part, without putting at risk the seal of the other screws 18 as, instead, in the case when these are brazed with eutectic alloy.

It is evident that the machine according to the invention offers the advantage of a high mobility, being much lighter and having a reduced bulkiness with respect to the conventional machines. In particular, the machine according to the invention may be easily moved with common elevators, may autonomously cover paths even of some hundreds of meters inside and outside a hospital, and may be transported with a suitably equipped vehicle from one clinic to another with no need of recalibration.

The present invention has been described, by way of illustration and not by way of limitation, according to its preferred embodiments, but it should expressly be understood that those skilled in the art can make other variations and/or changes, without so departing from the related scope of protection, as defined by the following claims.

What is claimed is:

1. A machine for intraoperative radiation therapy or IORT (Intra Operative Radio Therapy), the machine comprising:
a body, a radiating head connected to the body and configured to emit an electron beam, and a shield for X rays,
wherein said shield includes a mobile stand supporting an absorbing mass coupled, through a connecting device, to a detecting device configured to detect the position of the absorbing mass, and to give to a processor at least a signal indicating the position of the absorbing mass with respect to the body of the machine, said processor determining, on the basis of at least one of the position and the orientation of the radiating head, the position of the absorbing mass with respect to the electron beam axis,
the machine further comprising a system for measuring the total dose of the electron beam emitted during an IORT treatment for a period of duration R, and an amperometric transformer configured to measure an instantaneous current $I_{beam}$ of the emitted electron beam, an instantaneous dose D being calculated as a function of said instantaneous current $I_{beam}$, the total dose being calculated through a time integration of the instantaneous dose for the treatment period,
wherein said instantaneous dose D is calculated on the basis of a linear dependency from said instantaneous current $I_{beam}$, $$D = D_0 + A * \Delta I_{beam}$$

wherein $\Delta I_{beam} = I_{beam} - I_{beam\_Ref}$,
$I_{beam\_Ref}$ is a reference value of the instantaneous current of the emitted electron beam, and
$D_0$ and A are coefficients experimentally determined in a phase of clinical dosimetry of the machine.

2. The machine according to claim 1, wherein said detecting device includes two potentiometers configured to detect the azimuth angle and the distance of the center of the absorbing mass with respect to the body of the machine.

3. The machine according to claim 1, wherein said connecting device includes an anchorage dome of said detecting device.

4. The machine according to claim 1, wherein the mobile stand is provided with lockable wheels.

5. The machine according to claim 1, wherein the absorbing mass is mobile with respect to the mobile stand through a sliding device.

6. The machine according to claim 1, wherein said processor receiving at least a signal indicating the position of the absorbing mass with respect to the body of the machine is configured to drive a luminous signaling device for signaling necessary movements for correctly positioning the shield and attaining a correct position of the shield.

7. The machine according to claim 1, wherein said body is a mobile body, provided with at least two driving wheels and at least one idle wheel, each driving wheel being operated by a corresponding moving engine, the machine further comprising a handling device which is integral with the radiating head, and an engine for moving the radiating head, the engine being configured to impart to the radiating head at least a vertical translation motion, said handling device including at least three bidirectional sensors configured to measure both a traction stress and a compression stress, each one of the at least three bidirectional sensors sending to a control processor an electric signal which is proportional to a measured stress which is orthogonal to the sensor, said control processor operating the corresponding moving engine of each of said at least two driving wheels and the engine for moving the radiating head proportionally to the measured stress.

8. The machine according to claim 7, wherein said engine for moving the radiating head is configured to impart to the radiating head a rotational motion on at least a plane, said handling device including at least four bidirectional sensors, and said control processor operating the corresponding moving engine of each of said at least two driving wheels and the engine for moving the radiating head on the basis of an orientation of said handling device.

9. The machine according to claim 8, wherein said engine for moving the radiating head is configured to impart to the radiating head a pitch rotational motion and a roll rotational motion, and said handling device including at least five bidirectional sensors.

10. The machine according to claim 1, wherein the electron beam comes out from an accelerating structure, the machine further comprising a system for diffusing the electron beam leaving the accelerating structure, the system including a divergent magnetic lens configured to diverge the trajectory of the electron beam.

11. The machine according to claim 10, wherein said accelerating structure comprises a tuning device placed in corresponding slots of the accelerating structure, said tuning device being directly and locally welded to the accelerating structure onto each of said slots by electrical arc welding in a controlled atmosphere.

12. The machine according to claim 11, wherein the accelerating structure presents, in correspondence of each slot, a profile configured to dissipate heat.

13. The machine according to claim 11, wherein said tuning device includes a tuning screw covered by a cap.

* * * * *